United States Patent
McGee

(10) Patent No.: US 9,676,521 B2
(45) Date of Patent: Jun. 13, 2017

(54) BREATHING ASSIST DEVICE STORAGE COMPARTMENT ASSEMBLY

(71) Applicant: Daniel McGee, Harrisburg, PA (US)

(72) Inventor: Daniel McGee, Harrisburg, PA (US)

(*) Notice: Subject to any disclaimer, the term of this patent is extended or adjusted under 35 U.S.C. 154(b) by 0 days.

(21) Appl. No.: 14/859,528

(22) Filed: Sep. 21, 2015

(65) Prior Publication Data

US 2017/0081081 A1    Mar. 23, 2017

(51) Int. Cl.
*B65D 25/20* (2006.01)
*B65D 85/00* (2006.01)
*A61M 16/00* (2006.01)
*B65D 25/24* (2006.01)
*B60N 3/10* (2006.01)
*A47B 79/00* (2006.01)

(52) U.S. Cl.
CPC ............. *B65D 25/24* (2013.01); *A61M 16/00* (2013.01); *B65D 85/70* (2013.01); *A47B 79/00* (2013.01); *A61M 2209/06* (2013.01); *B60N 3/103* (2013.01)

(58) Field of Classification Search
CPC .......... B60N 3/103; B60N 1/04; B60R 11/00; A47B 79/00; A47B 81/00; A47B 81/02; A47B 96/00; B65D 25/20; B65D 85/00; B65D 85/70; A61M 16/00; A61M 2209/06
USPC ........... 248/311.2, 312.1, 690, 693; 220/482, 220/737, 23.4, 23.86, 480; 312/242, 312/293.2, 293.1, 321.5; 206/750, 45.23
See application file for complete search history.

(56) References Cited

U.S. PATENT DOCUMENTS

| | | | | |
|---|---|---|---|---|
| 3,442,371 A | * | 5/1969 | Deshong | B65D 11/00 206/45.23 |
| 4,663,621 A | * | 5/1987 | Field | G07C 9/0069 221/154 |
| 4,718,550 A | * | 1/1988 | Johnson | G11B 23/023 206/387.13 |
| 4,779,431 A | * | 10/1988 | Burk | D06F 13/02 68/12.16 |
| 5,181,555 A | * | 1/1993 | Chruniak | B60N 3/103 224/483 |
| 6,301,501 B1 | * | 10/2001 | Cronin | A61N 1/3931 200/61.62 |
| D592,435 S | | 5/2009 | Jasman | |
| 7,766,294 B2 | * | 8/2010 | Schimmeyer | B60N 3/103 220/482 |
| 7,931,021 B2 | | 4/2011 | Livingston et al. | |
| 8,282,050 B2 | | 10/2012 | Georgey | |

(Continued)

FOREIGN PATENT DOCUMENTS

WO    WO9927818    6/1999

*Primary Examiner* — Tan Le

(57) ABSTRACT

A breathing assist device storage compartment assembly includes a housing having a rear wall and a perimeter wall attached thereto and extending forward of the rear wall. The perimeter wall includes a top wall, a bottom wall, a first side wall and a second side wall. A front side of the housing is open. A support is attached to the housing and engages the top wall adjacent to front side. The support engages furniture at an edge thereof such that the housing extends downwardly from the edge of the furniture and the furniture closes the front side. The support is hingedly coupled to the housing to allow the housing to pivot with respect to the support and facilitate access into an interior of the housing, wherein a breathing assist device is positioned.

2 Claims, 6 Drawing Sheets

(56) References Cited

U.S. PATENT DOCUMENTS

| | | | |
|---|---|---|---|
| 8,297,443 B2 * | 10/2012 | Ogando | B65D 5/4208 |
| | | | 206/45.23 |
| 8,387,934 B2 | 3/2013 | Nally et al. | |
| 8,397,647 B1 | 3/2013 | Riegel | |
| D690,059 S * | 9/2013 | Robbins | D30/161 |
| 2008/0078397 A1 | 4/2008 | Scott et al. | |
| 2008/0185359 A1 | 8/2008 | Baxter | |
| 2015/0076144 A1 * | 3/2015 | Chalifoux | B65D 5/3692 |
| | | | 220/6 |

\* cited by examiner

BREATHING ASSIST DEVICE STORAGE COMPARTMENT ASSEMBLY

BACKGROUND OF THE DISCLOSURE

Field of the Disclosure

The disclosure relates to furniture mounted storage devices and more particularly pertains to a new furniture mounted storage device for storing breathing assist devices adjacent to a person's bed such that the breathing assist device is easily accessible and stored in a hygienic manner.

SUMMARY OF THE DISCLOSURE

An embodiment of the disclosure meets the needs presented above by generally comprising a housing having a rear wall and a perimeter wall attached thereto and extending forward of the rear wall. The perimeter wall includes a top wall, a bottom wall, a first side wall and a second side wall. A front side of the housing is open. A support is attached to the housing and engages the top wall adjacent to front side. The support engages furniture at an edge thereof such that the housing extends downwardly from the edge of the furniture and the furniture closes the front side. The support is hingedly coupled to the housing to allow the housing to pivot with respect to the support and facilitate access into an interior of the housing, wherein a breathing assist device is positioned.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
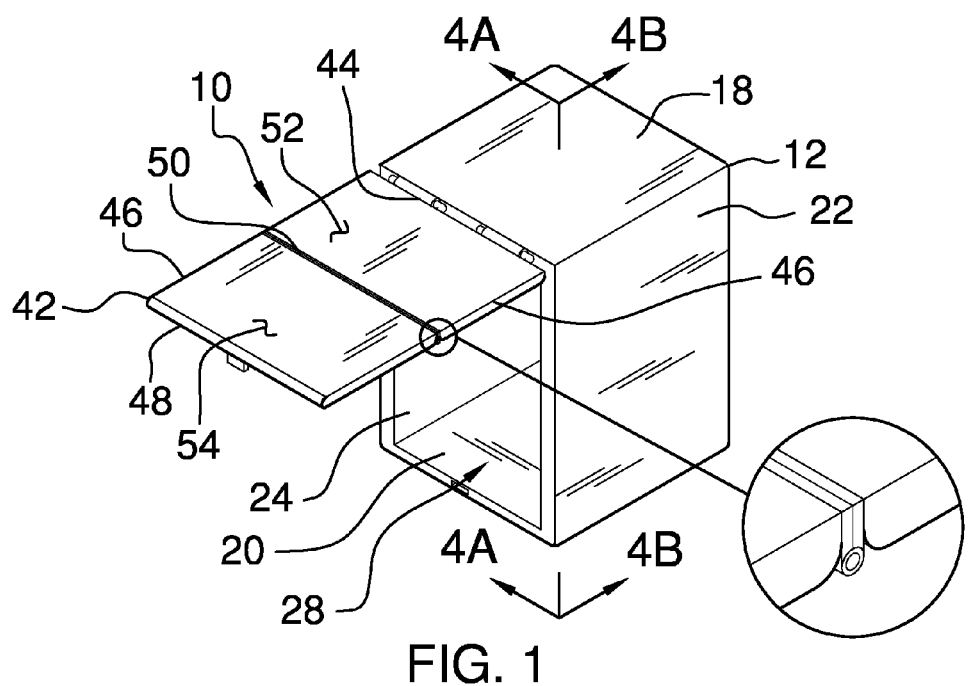
FIG. 1 is a front perspective view of a breathing assist device storage compartment assembly according to an embodiment of the disclosure.
Figure 2:
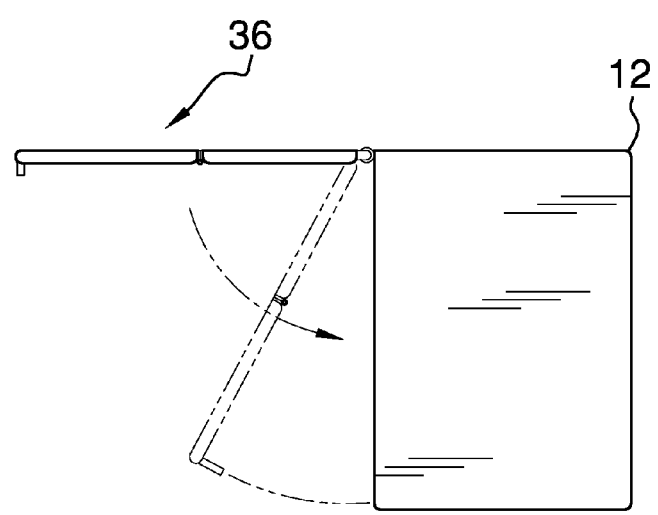
FIG. 2 is a side view of an embodiment of the disclosure.

With reference now to the drawings, and in particular to FIGS. 1 through 7 thereof, a new furniture mounted storage device embodying the principles and concepts of an embodiment of the disclosure and generally designated by the reference numeral 10 will be described.

As best illustrated in FIGS. 1 through 7, the breathing assist device storage compartment assembly 10 generally comprises a housing 12 that has a rear wall 14 and a perimeter wall 16 attached to and extending forward of the rear wall 14. The perimeter wall 16 includes a top wall 18, a bottom wall 20, a first side wall 22 and a second side wall 24. A front side 26 of the housing 12 remains open and will function as an access into an interior 28 of the housing 12. A mount 30 is attached to an inner surface of the rear wall 14 and is configured to engage a breathing assisting device. The mount 30 may comprise a protuberance which acts as a female mount for engaging a face mask 32 of the breathing assisting device which may be a CPAP (continuous positive airway pressure device), or similar such as a BiPAP, used by people to assist them breathe while sleeping. The mount 30 may be comprised of a resiliently compressible material to frictionally engage the face mask 32. This will keep the face mask 32 within a clean environment as opposed to its placement on a countertop or nightstand, which may be unsanitary, and more importantly prevent its falling onto a floor surface. The rear wall 14 may have one or more apertures 34 extending therethrough so that if needed the housing 12 may receive a hook, nail or other conventional mounting bracket used for supporting the housing 12 on a wall surface. However, this method of mounting is not preferred as will be understood below.

A support 36 is attached to the housing 12 and engages the top wall 18 adjacent to front side 26. The support 36 is configured to engage furniture 38 at an edge 40 thereof such that the housing 12 extends downwardly from the edge 40 of the furniture 38 and the furniture 38 closes the front side 26. The support 36 is hingedly coupled to the housing 12 to allow the housing 12 to pivot with respect to the support 36 and facilitate access into an interior 28 of the housing 12.

With more particularity, the support 36 includes a panel 42 having a top edge 44 that is hingedly coupled to the top wall 18 adjacent to the front side 26. The panel 42 is pivotally positioned in a closed position closing the front side 26 or in an open position exposing the front side 26. The panel 42 includes a pair of lateral edges 46 and a distal edge 48. The distal edge 48 is positioned opposite of the top edge 44. The panel 42 has a break 50 therein extending through the lateral edges 46 and is oriented parallel to the top edge 44 to define an upper portion 52 including the top edge 44 and a lower portion 54 including the distal edge 48. The upper 52 and lower 54 portions are hingedly coupled together. The lower portion 54 and the upper portion 52 may be angled with respect to each other such that the panel 42 is configured to engage an edge 40 of furniture 40 wherein the front side 26 abuts the furniture 40.

Figure 3:
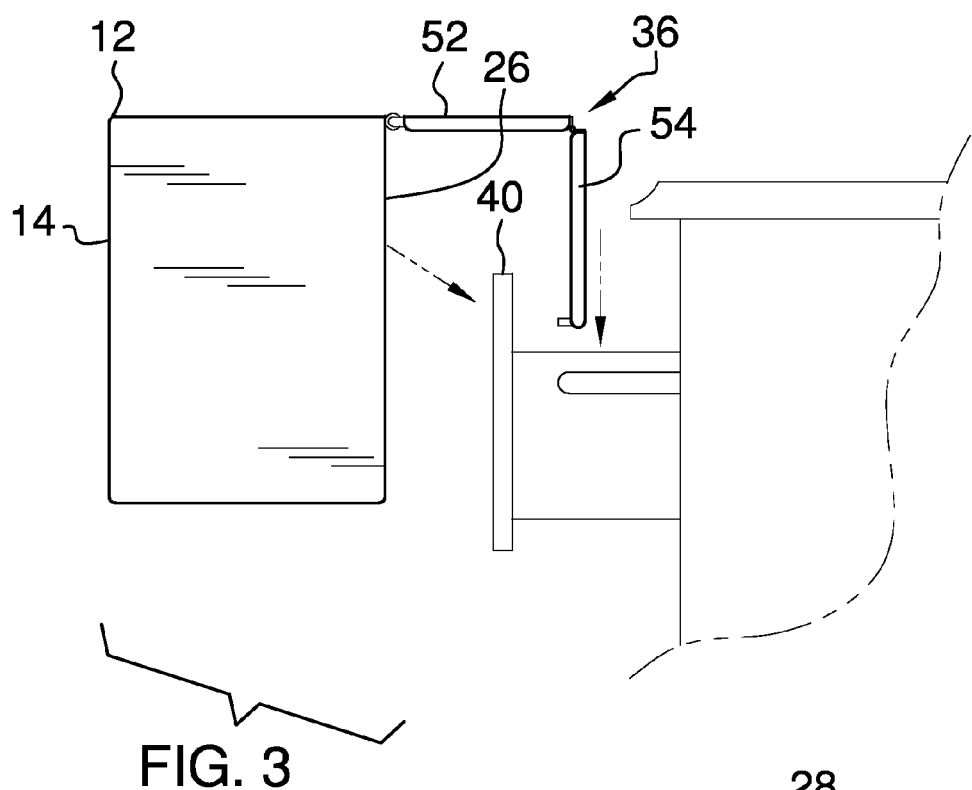
FIG. 3 is a side view of an embodiment of the disclosure.
Figure 4A:
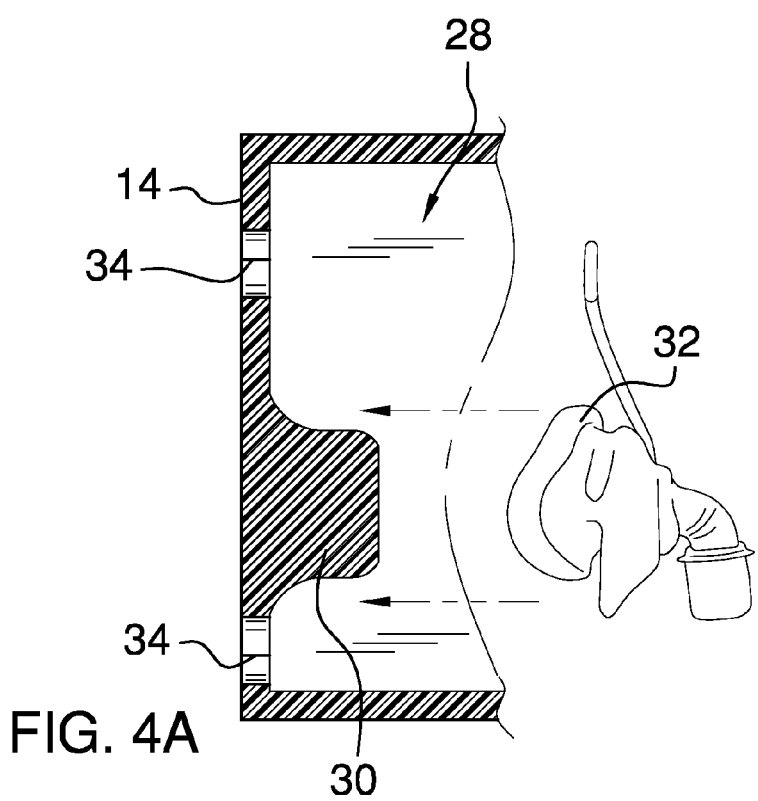
FIG. 4A is a cross-sectional view of an embodiment of the disclosure taken along line 4A-4A of FIG. 1.
Figure 4B:
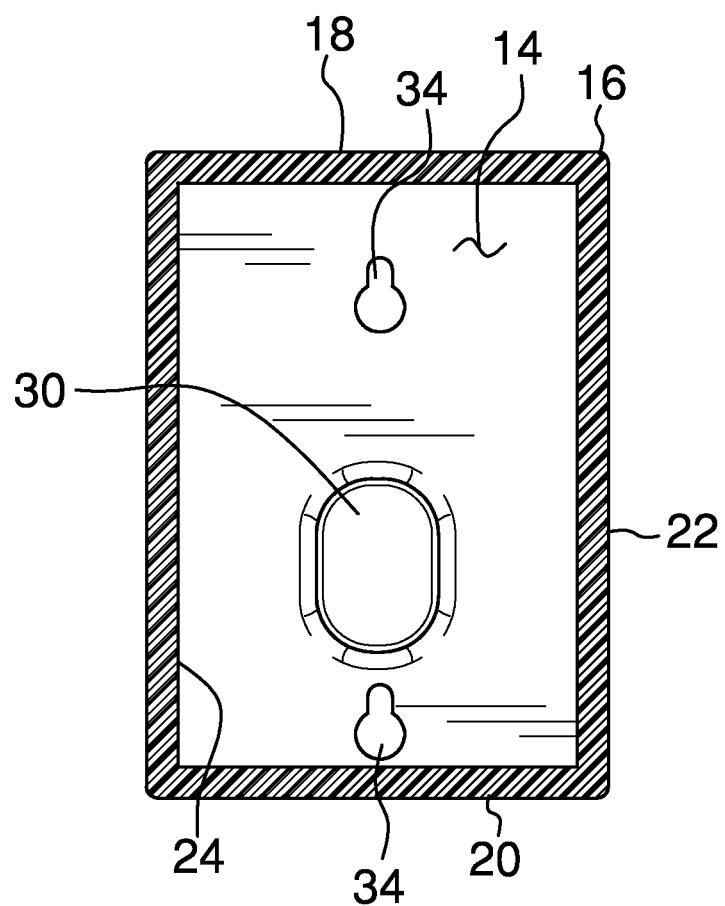
FIG. 4B is a cross-sectional view of an embodiment of the disclosure taken along line 4B-4B of FIG. 1.
Figure 5:
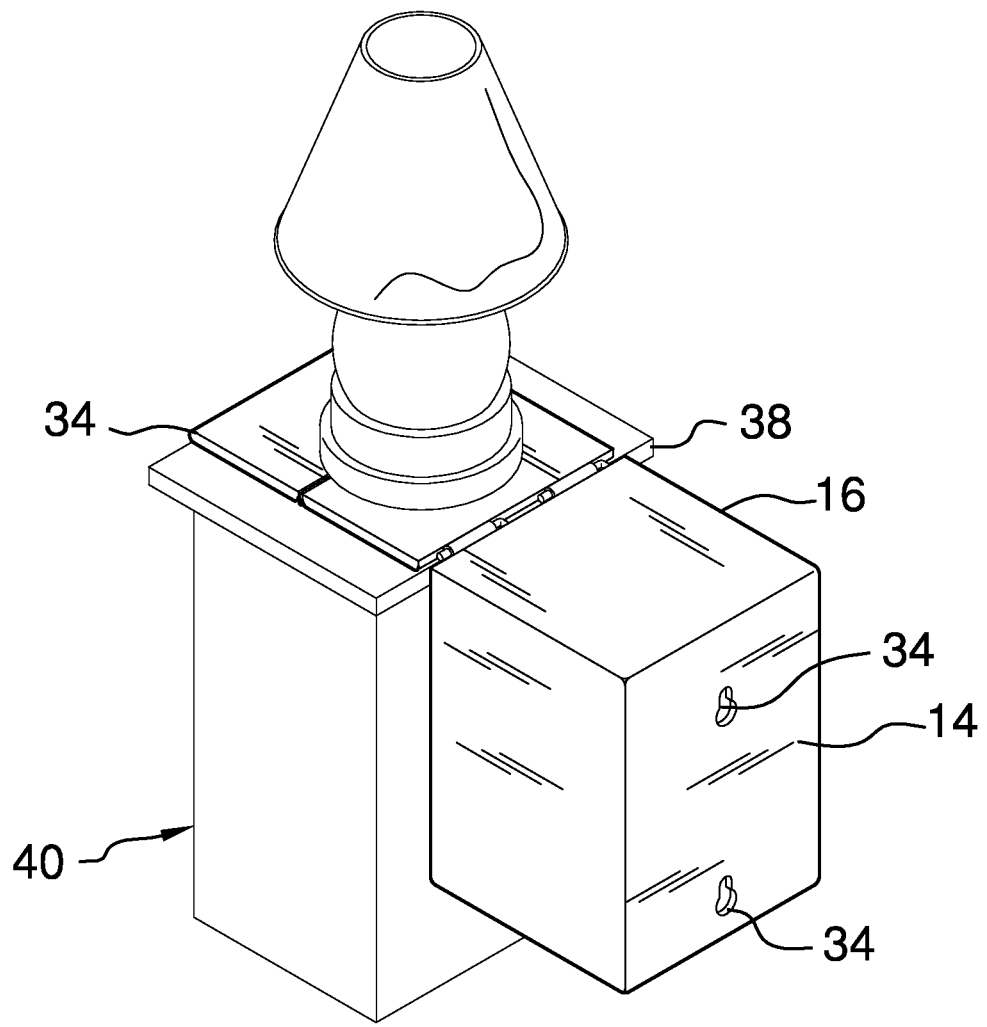
FIG. 5 is a perspective rear view of an embodiment of the disclosure.
Figure 6:
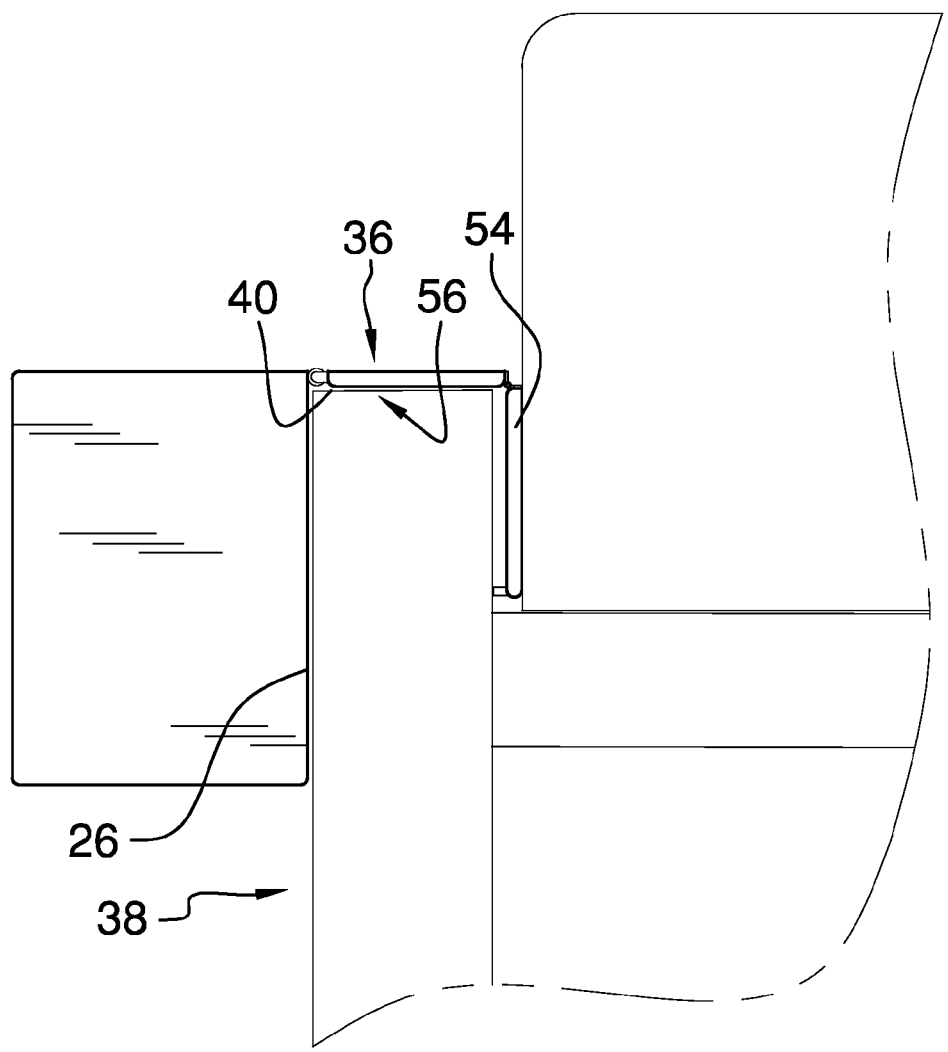
FIG. 6 is a side view of an embodiment of the disclosure.
Figure 7:
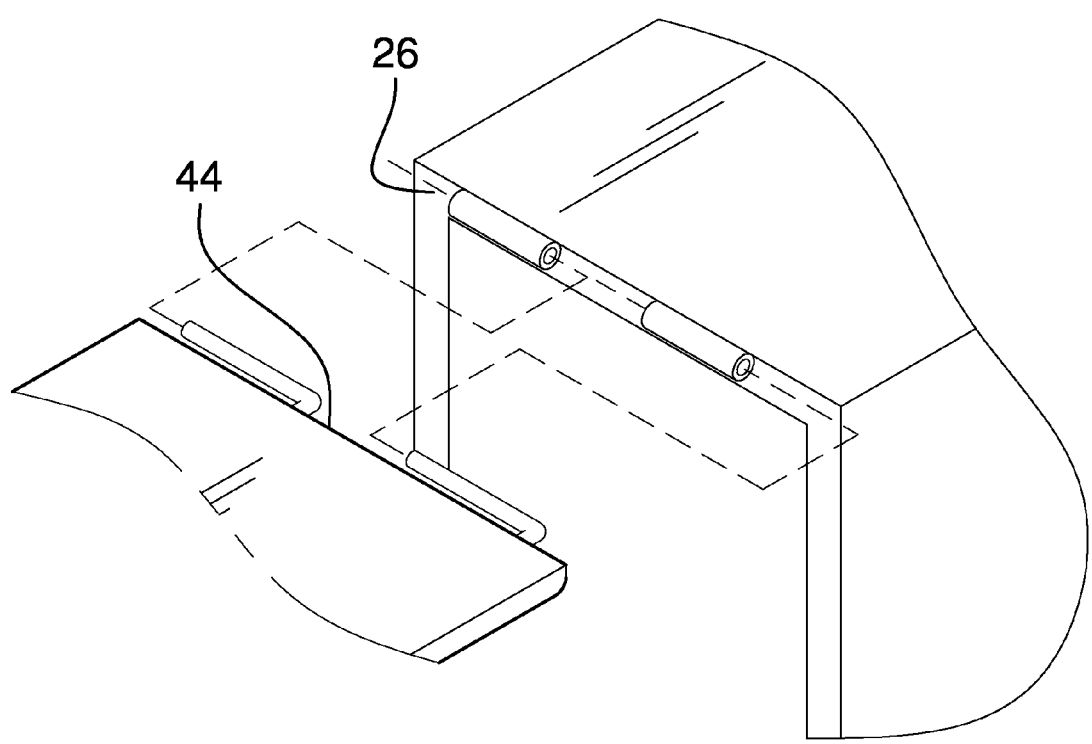
FIG. 7 is an exploded view of an embodiment of the disclosure.

As can be seen in the Figures, the support 36 may be used in multiple configurations. FIG. 3 depicts the lower portion 54 being extended into a drawer whereupon the drawer will be closed such that the housing 12 and upper portion 52 extend down from the top edge 40 of the front of the drawer. FIG. 5 teaches the upper 52 and lower 54 portions each extending across the top of a nightstand, or bed side table, such that a counterweight may be positioned on the panel 42 to retain the housing 12 in abutment with the nightstand. In this case the counterweight is shown to be a lamp but other articles may be utilized which are typically positioned on a nightstand. FIG. 6 shows the upper 52 and lower 54 portions being retained at a perpendicular angle with respect to each other such that a channel 56 is formed between the lower portion 54 and the front side 26 to receive headboard or sideboard of a bed. In each case, the housing 12 is closed by the article of furniture 40 so that the facemask 32 is retained within the housing 12 while also being positioned for easy access by the user of the facemask 32.

In use, the user places the housing 12 where desired on a piece of furniture 40 such as described herein and in FIGS. 3, 5 and 6. The housing 12 is pivoted relative to the furniture 40 to open or close the front side 26 of the housing 12 so that the facemask 32 of the breathing assisting device may be positioned in or removed from the housing 12.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A storage assembly for a breathing assist device configured for being positioned on an article of furniture, said storage assembly including:
   a housing having a rear wall and a perimeter wall, said perimeter wall being attached to and extending forward of said rear wall, said perimeter wall including a top wall, a bottom wall, a first side wall and a second side wall, a front side of said housing being open, wherein said rear wall has at least one aperture extending therethrough;
   a support being attached to said housing, said support engaging said top wall adjacent to front side, said support being configured to engage furniture at an edge thereof such that said housing extends downwardly from the edge of the furniture and said furniture closes said front side, said support being hingedly coupled to said housing to allow said housing to pivot with respect to said support and facilitate access into an interior of said housing;
   a mount being attached to and extending from an inner surface of said rear wall and being configured to engage a breathing assisting device; and
   wherein said support includes a panel having a top edge being hingedly coupled to said top wall adjacent to said front side, said panel being pivotally positioned in a closed position closing said front side or in an open position exposing said front side, said panel including a pair of lateral edges and a distal edge, said distal edge being positioned opposite of said top edge, said panel having a break therein extending through said lateral edges and being oriented parallel to said top edge to define an upper portion including said top edge and a lower portion including said distal edge, said upper and lower portions being hingedly coupled together, said lower portion and said upper portion being angled with respect to each other such that said panel is configured to engage an edge of furniture wherein said front side abuts the furniture.

2. A storage assembly for a breathing assist device configured for being positioned on an article of furniture, said storage assembly including:
   a housing having a rear wall and a perimeter wall, said perimeter wall being attached to and extending forward of said rear wall, said perimeter wall including a top wall, a bottom wall, a first side wall and a second side wall, a front side of said housing being open;
   a support being attached to said housing, said support engaging said top wall adjacent to front side, said support being configured to engage furniture at an edge thereof such that said housing extends downwardly from the edge of the furniture and said furniture closes said front side, said support being hingedly coupled to said housing to allow said housing to pivot with respect to said support and facilitate access into an interior of said housing, said support including:
   a panel having a top edge being hingedly coupled to said top wall adjacent to said front side, said panel being pivotally positioned in a closed position closing said front side or in an open position exposing said front side, said panel including a pair of lateral edges and a distal edge, said distal edge being positioned opposite of said top edge, said panel having a break therein extending through said lateral edges and being oriented parallel to said top edge to define an upper portion including said top edge and a lower portion including said distal edge, said upper and lower portions being hingedly coupled together, said lower portion and said upper portion being angled with respect to each other such that said panel is configured to engage an edge of furniture wherein said front side abuts the furniture;
   a mount being attached to and extending from an inner surface of said rear wall and being configured to engage a breathing assisting device; and
   said rear wall having at least two apertures extending therethrough.

* * * * *